US011957740B2

(12) United States Patent
Singh et al.

(10) Patent No.: US 11,957,740 B2
(45) Date of Patent: Apr. 16, 2024

(54) COMPLEX OF BOTULINUM NEUROTOXIN E AND ITS BINDING PROTEIN AS A FORMULATION WITH ENHANCED POTENCY

(71) Applicant: Prime Bio, Inc., North Dartmouth, MA (US)

(72) Inventors: Bal Ram Singh, Dartmouth, MA (US); Raj Kumar, Dartmouth, MA (US)

(73) Assignee: Prime Bio, Inc., North Dartmouth, MA (US)

( * ) Notice: Subject to any disclaimer, the term of this patent is extended or adjusted under 35 U.S.C. 154(b) by 131 days.

(21) Appl. No.: 17/200,822

(22) Filed: Mar. 13, 2021

(65) Prior Publication Data
US 2022/0288173 A1 Sep. 15, 2022

(51) Int. Cl.
*A61K 38/48* (2006.01)
*C07K 1/14* (2006.01)
*C07K 1/18* (2006.01)

(52) U.S. Cl.
CPC .......... *A61K 38/4893* (2013.01); *C07K 1/145* (2013.01); *C07K 1/18* (2013.01)

(58) Field of Classification Search
None
See application file for complete search history.

(56) References Cited

U.S. PATENT DOCUMENTS

| 6,699,966 B1 | 3/2004 | Singh et al. |
| 2020/0046814 A1 | 2/2020 | Abushakra et al. |

OTHER PUBLICATIONS

Binz, T., Kurazono, H., Popoff, M.R., Eklund, M. W., Sakaguchi, G., Kozaki, S., Krieglstein, K., Henschen, A,, Gill, M. D.,and Niemann,H. (1990b) Nucleic Acids Res. 18, 5556.
Binz T, Kurazono H, Wille M, Frevert J, Wernars K, Niemann H. The complete sequence of botulinum neurotoxin type A and comparison with other clostridial neurotoxins. J Biol Chem. 1990a; 265:9153-9158.
Kumar, R., Chang, T. W., and Singh, B. R. (2013) Evolutionary traits of toxins. Handbook of Toxinology (Editor: P. Gopalakrishnakone, Springer): Biological Toxins and Bioterrorism, Springer Dordrecht Heidelberg New York London, vol. 1, chapter 23, 527-557.
Hauser, D., Eklund, M. W., Kurazono, H., Binz, T., Niemann, H., Gill, M. D., Boquet, P., and Popoff, M. R. (1990) Nucleic Acids Res. 18,4924.
Ohishi, I., and Sakaguchi, G. (1980). Oral toxicities of Clostridium botulinum type C and D toxins of different molecular sizes. Infect Immun. May 1980; 28(2): 303-309.
Ohishi, I., Sugii, S., and Sakaguchi, G. (1977). Oral toxicities of Clostridium botulinum toxins in response to molecular size. Infect Immun., 16, 107-109.
Sakaguchi G, 1983, Clostridium botulinum toxins, Pharmac Therap., 19:165-194.
Singh, B. R., and DasGupta, B. R. (1989). Molecular topography and secondary structure comparisons of botulinum neurotoxin types A, B, and E. Mol Cell Biochem, 86, 87-95.
Singh, B. R., Foley, J., and Lafontaine, C. (1995). Physiological and immunological characterization of type E botulinum neurotoxin binding protein purified from Clostridium botulinum. Journal of physical chemistry, 14, 7-18.
Singh, B. R., Gimenez, J. A., and DasGupta, B. R. (1991). Comparative molecular topography of botulinum neurotoxins from Clostridium butyricum and Clostridium botulinum type E. Biochim Biophys Acta, 1077, 119-126.
Sugii S and Sakaguchi G: Molecular construction of Clostridium botulinum type A toxins. Infect immune 1975. 12:1262-70.
Thompson, D. E., Brehm, J. K., Oultram, J. D., Swinfield, T. J., Shone, C. C., Atkinson, T., Melling, J., and Minton, N. P. (1990). The complete amino acid sequence of the Clostridium botulinum type A neurotoxin, deduced by nucleotide sequence analysis of the encoding gene. European Journal of Biochemistry, Apr. 20, 1990;189(1):73-81.
Whelan SM, Elmore MJ, Bodsworth NJ, Atkinson T, Minton N (1992a) The complete amino acid sequence of the Clostridium botulinum type E neurotoxin, deduced by nucleotide sequence analysis of the encoding gene. Eur J Biochem 204:657-667.
Whelan, S., Elmore, M. J., Bodsworth, N., Brehm, J, Atkinson, T., and Minton, N. P. (1992 b). Molecular Cloning of the Clostridium botulinum Structural Gene Encoding the Type B Neurotoxin and Determination of Its Entire Nucleotide Sequence. Applied and Environment Microbiology, 58, 2345-2354.
Eswaramoorthy et al. (2015) Molecular Assembly of Clostridium botulinum progenitor M complex of type E. Scientific Reports. 5, 17795: 1-9.

(Continued)

*Primary Examiner* — Brian Gangle

(57) ABSTRACT

Compositions comprising the L complex or the M complex of the botulinum neurotoxin E with its associated neurotoxin binding protein(s) (NBP), methods of making, and methods of use to treat pain and wrinkles by injecting locally. Methods of making and isolating the L and M complex comprise a multi-step process of: providing a bacterial cultured media comprising the complex of botulinum neurotoxin E and neurotoxin binding proteins; centrifuging and pelletizing the cultured media; stirring the pelletized culture at 0 to 10° C. over a period of 4 to 24 hours; centrifuging the stirred solution to obtain a supernatant; precipitating the supernatant and filtering to obtain the precipitate; and dissolving the precipitate, centrifuging and filtering to obtain a solution comprising M complex and/or L complex of botulinum neurotoxin E and its NBP; and passing the solution through a functionalized sephadex ion exchange column to isolate the complex.

8 Claims, 3 Drawing Sheets

(56) References Cited

OTHER PUBLICATIONS

Schantz EJ, Johnson EA (1992) Properties and use of botulinum toxin and other microbial neurotoxins in medicine. Microbiology and Molecular Biology Reviews. 56(1): 80-99.

Sharma SK, Singh BR (2004) Enhancement of the Endopeptidase Activity of Purified Botulinum Neurotoxins A and E by an Isolated Component of the Native Neurotoxin Associated Proteins. Biochemistry. 43: 4791-4798.

Li, B., Qian, X., Sarkar, H. K., and Singh, B. R. (1998) Molecular characterization of type E Clostridium botulinum and comparison to other types of Clostridium botulinum, Biochimica et Biophysica. Acta. 1395, 21-27.

*Prior Art*

COMPLEX OF BOTULINUM NEUROTOXIN E AND ITS BINDING PROTEIN AS A FORMULATION WITH ENHANCED POTENCY

FIELD OF THE INVENTION

The presently claimed invention is directed to a composition comprising a complex of botulinum neurotoxin E and a neurotoxin binding protein, and its method of use in a therapeutic field. The application also discloses a method for the isolation of a complex of botulinum neurotoxin E and a neurotoxin binding protein. In particular, the presently claimed invention is directed to a composition comprising a L complex or a M complex of the botulinum neurotoxin E and one neurotoxin binding protein (NBP), and its method of use in therapeutic and cosmetics field.

BACKGROUND OF THE INVENTION

The present invention relates to systems and processes for obtaining a complex comprising a Clostridial neurotoxin E and its binding protein, methods for making a pharmaceutical composition therefrom and to therapeutic and cosmetic uses of the pharmaceutical composition so made.

A pharmaceutical composition suitable for administration to a human or animal for a therapeutic, diagnostic, research or cosmetic purpose comprises an active ingredient and one or more excipients, buffers, carriers, stabilizers, tonicity adjusters, preservatives and/or bulking agents. The active ingredient in a pharmaceutical composition can be a biologic, such as a botulinum neurotoxin.

The genus *Clostridium* has more than one hundred and twenty-seven species, grouped by morphology and function. The anaerobic, gram positive bacterium *Clostridium botulinum* produces a potent polypeptide neurotoxin, botulinum toxin (synonymously "toxin"), which causes a neuroparalytic illness in humans and animals known as botulism. Symptoms of botulinum toxin intoxication can progress from difficulty walking, swallowing, and speaking to paralysis of the respiratory muscles and death.

One unit of botulinum toxin is defined as the $LD_{50}$ upon intraperitoneal injection into female Swiss Webster mice weighing about 18-20 grams each. One unit of botulinum toxin is the amount of botulinum toxin that kills 50% of the mice. Seven generally immunologically distinct botulinum neurotoxins have been characterized, these being respectively botulinum neurotoxin serotypes A, B, $C_1$, D, E, F and G, each of which is distinguished by neutralization with type-specific antibodies. The different serotypes of botulinum toxin vary in the animal species that they affect and, in the severity, and duration of the paralysis they evoke. The botulinum toxins apparently bind with high affinity to cholinergic motor neurons and translocate into the neuron and block the presynaptic release of acetylcholine.

Botulinum toxins have been used in clinical settings for the treatment of e.g. neuromuscular disorders characterized by hyperactive skeletal muscles. Botulinum toxin type A has been approved by the U.S. Food and Drug Administration (FDA) for the treatment of essential blepharospasm, strabismus and hemifacial spasm in patients over the age of twelve, cervical dystonia, glabellar line (facial) wrinkles and for treating hyperhidrosis. The FDA has also approved a botulinum toxin type B for the treatment of cervical dystonia.

Although all the botulinum toxins serotypes apparently inhibit release of the neurotransmitter acetylcholine at the neuromuscular junction, they do so by affecting different neurosecretory proteins and/or cleaving these proteins at different sites. Botulinum toxin type A is a zinc endopeptidase that can specifically hydrolyze a peptide linkage of the intracellular, vesicle-associated protein (VAMP, also called synaptobrevin), which is a 25 kiloDalton (kDa) synaptosomal associated protein (SNAP-25). Botulinum type E also cleaves SNAP-25, but it targets different amino acid sequences within this protein as compared to botulinum toxin type A. Botulinum toxin types B, D, F and G act on VAMP with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

The molecular weight of the active botulinum toxin protein molecule (also known as "pure toxin" or as the "neurotoxic component" from a botulinum toxin complex) for all seven of the known botulinum toxin serotypes is about 150 kDa. Interestingly, the botulinum toxins are released by Clostridial bacterium as complexes comprising the 150 kDa neurotoxic component along with one or more associated non-toxin proteins. Thus, the botulinum toxin type A complex can be produced by Clostridial bacterium as 900 kDa (LL complex), 500 kDa (L complex) and 300 kDa (M complex) forms (approximate molecular weights). Botulinum toxin types B and $C_1$ are apparently produced as only a 500 kDa complex. Botulinum toxin type D is produced as both 300 kDa and 500 kDa complexes. Finally, botulinum toxin types E 500 kDa and 300 kDa, and F are produced as only approximately 300 kDa complexes. The complexes (i.e. molecular weight greater than about 150 kDa) contain hemagglutinin (HA) proteins and a non-toxin non-hemagglutinin (NTNH) protein. Thus, a botulinum toxin complex can comprise a botulinum toxin molecule (the neurotoxic component) and one or more HA proteins and/or the NTNH protein. These two types of non-toxin proteins (which along with the botulinum toxin molecule can comprise the relevant neurotoxin complex) may act to provide stability against denaturation to the botulinum toxin molecule and protect it against digestive acids when the toxin is ingested. Additionally, it is possible that the larger (greater than about 150 kDa molecular weight) botulinum toxin complexes may result in a slower rate of diffusion of the botulinum toxin away from a site of intramuscular injection of a botulinum toxin complex. The success of botulinum toxin type A to treat a variety of clinical conditions has led to interest in other botulinum toxin serotypes. Thus, at least botulinum toxins types A and B have been used clinically in humans. Additionally, a formulation of the neurotoxic component (i.e. without the associated non-toxin proteins) is sold in Europe under the tradename XEOMIN™ (Merz Pharmaceuticals®, Frankfurt, Germany).

A commercially available botulinum toxin containing pharmaceutical composition is sold under the trademark BOTOX® (botulinum toxin type A purified neurotoxin complex) available commercially from Allergan®, Inc., of Irvine, Calif. Each 100 units vial of BOTOX® consists of about 5 ng of purified botulinum toxin type A complex, 0.5 mg human serum albumin, and 0.9 mg sodium chloride, in a vacuum-dried form and is intended for reconstitution with sterile normal saline without a preservative (0.9% sodium chloride injection). Other commercially available, botulinum toxin-containing pharmaceutical compositions include Dysport® (*Clostridium botulinum* type A toxin hemagglutinin complex with human serum albumin and lactose in the botulinum toxin pharmaceutical composition), available from Ipsen Limited®, Berkshire, U.K. as a powder to be reconstituted with 0.9% sodium chloride before use), and MyoBloc® (an injectable solution comprising botulinum toxin type B, human serum albumin, sodium succinate, and sodium chloride at about pH 5.6, available from Solstice Neurosciences® of San Diego, Calif. The neurotoxic component (the 150 kDa toxin molecule) and botulinum toxin complexes (300 kDa to 900 kDa) can be obtained from, for example, List Biological Laboratories®, Inc., Campbell, Calif.; the Centre for Applied Microbiology and Research®, Porton Down, U.K.; Wako (Osaka, Japan), as well as from Sigma Chemicals® of St Louis, Mo.

Oral toxicity of botulinum neurotoxin is dependent upon directly or indirectly associated nontoxic proteins (Sakaguchi, 1983; Ohishi et al., 1977; Ohishi and Sakaguchi, 1980), which together they form a complex form of protein. Depending upon the number of associated proteins complexed with it, the neurotoxin complex exists as 19S (LL), 16S (L), and 12S (M) molecular species. In bacterial cultures, type A botulinum neurotoxin exists as LL, L, and M forms, whereas type E neurotoxin exists in L and M forms (Sakaguchi, 1983; Sugii and Sakaguchi, 1975). The complexes of the other serotypes of botulinum neurotoxin range between 12S and 19S subunits, with 12S being the smallest subunit of a complex for any of the serotypes (Sakaguchi, 1983). All serotypes of botulinum neurotoxin (a 7S subunit) can be dissociated from the rest of the associated proteins under alkaline pH conditions (Sakaguchi, 1983).

The neurotoxins are produced as single-chain polypeptides, but are generally nicked at one-third the position from the N-terminus (due to reduction in disulfide bond between heavy and light chain) to produce the light and heavy chains. The genes responsible for expressing the neurotoxins have been cloned and sequenced for types A, B, C1, D, E, and F in the past few years (Binz et al., 1990a, b; Hauser et al., 1990; Thompson, et al., 1990; Whelan et al., 1992a,b). Recent reports from Oguma and co-workers have suggested that genes for both the type E botulinum neurotoxin and its associated protein are regulated by the same set of operators and promotors, thus indicating that their association may serve a specific purpose, which has evolved over time (Kumar et al., 2013). Because of such specificity, we call the associated protein the neurotoxin binding protein or NBP. Compared to intraperitoneal injection, the oral toxicity of the 7S neurotoxin (corresponding to 150-kDa pure neurotoxin) is virtually nonexistent. However, its oral toxicity increases with the size of its complex with associated proteins (Sakaguchi, 1983). It appears that the associated proteins play a role in preserving toxicity of the ingested neurotoxin, but the molecular mechanisms involved are not known. An understanding of such mechanisms could not only explain the basis of the toxico-infection of food poisoning by botulinum neurotoxins, but it could also provide clues to the designing of oral vaccines because this is perhaps the only known natural system where a group of proteins protect another protein from the digestive system. In order to understand the molecular basis of the neurotoxin protection by its associated protein, initial steps would involve isolation and characterization of the associated proteins and analysis of their binding to the neurotoxin.

There has been increased interest in the botulinum neurotoxin type E recently, as it has been reported to act much faster than the type A (R. Eleopra et al./Neuroscience Letters 256 (1998) 135-138). The patent application US 2020/0046814 A1 discloses a composition comprising botulinum neurotoxin E and its use in therapy, especially in cosmetic therapy. It is known that the oral toxicity of botulinum neurotoxin is dependent upon additional nontoxic proteins in association with it (Sakaguchi, 1983; Ohishi et al., 1977; Ohishi and Sakaguchi, 1980).

As illustrated in the prior art diagram of FIG. 1A, type E botulinum neurotoxin is produced by the *Clostridium botulinum* type E strain, along with five other proteins, all coded by a cluster of genes. These proteins when expressed in a bacterial cell spontaneously form a type E botulinum neurotoxin complex (BoNT/EC), also referred to as the Large or the "L-complex". The BoNT/EC protein complex comprises: 150 (BoNT/E), 120 (NBP), 80 (NAP-80), 60 (NAP-60), 40 (NAP-40), and 18 kDa (NAP-18) (Li et al., 1998; Singh et al., 1995; Singh and Zhang, 2004).

It is possible to separate the type E neurotoxin bound to only the neurotoxin binding protein (NBP) to form a two-protein complex, referred to as the Medium or the "M-Complex". And as illustrated in the prior art diagram of FIG. 1B, this M-Complex comprises the BoNT/E protein and the NBP.

Therefore, there is a need within the industry for improved formulations of botulinum neurotoxin to provide stability against denaturation to the botulinum toxin molecule and to protect it during storage, and against digestive acids when the toxin is ingested; and preferably comprising the L-complex or the M-complex of type E botulinum neurotoxin.

SUMMARY OF THE INVENTION

The presently claimed invention comprises a process for the isolation of, and a composition comprising: the complex of botulinum neurotoxin E and its associated binding proteins, especially the isolation of the L complex of botulinum neurotoxin E and its associated binding proteins; and the M complex of botulinum neurotoxin E (FIG. 2) and its associated neurotoxin binding protein. The presently claimed invention is a fast-acting and more potent, improved composition comprising a complex of botulinum neurotoxin E and its associated neurotoxin binding protein for use as pharmaceutical and/or cosmetic composition.

Accordingly, the first aspect of the presently claimed invention is directed to a formulation comprising a complex of pure botulinum neurotoxin E and its neurotoxin binding protein.

The second aspect of the presently claimed invention is directed to a formulation comprising the L complex of botulinum neurotoxin E.

The third aspect of the presently claimed invention is directed to a formulation comprising the M complex of botulinum neurotoxin E.

The fourth aspect of the presently claimed invention is directed to a method for the isolation of a complex of botulinum neurotoxin E and its neurotoxin binding protein.

The fifth aspect of the presently claimed invention is directed to a method for the isolation of the L complex of botulinum neurotoxin E.

The sixth aspects of the presently claimed invention is directed to method for the isolation of the M complex of botulinum neurotoxin E.

The seventh aspect of the presently claimed invention is directed to the use of the formulation comprising a complex of botulinum neurotoxin E and its neurotoxin binding protein/s in cosmetics.

The eighth aspect of the presently claimed invention is directed to the use of the formulation comprising the L complex of botulinum neurotoxin E in cosmetics.

The ninth aspect of the presently claimed invention is directed to the use of the formulation comprising the M complex of botulinum neurotoxin E in cosmetics.

The tenth aspect of the presently claimed invention is directed to the use of the formulation comprising a complex of botulinum neurotoxin E as a pharmaceutical composition.

The eleventh aspect of the presently claimed invention is directed to the use of the composition comprising the L complex of botulinum neurotoxin E as a pharmaceutical composition.

The twelfth aspect of the presently claimed invention is directed to the use of the formulation comprising the M complex of botulinum neurotoxin E as a pharmaceutical composition.

The thirteenth aspect of the presently claimed invention is directed a method of treating wrinkles in the skin using a formulation comprising a complex of botulinum neurotoxin E.

The fourteenth aspect of the presently claimed invention is directed a method of treating wrinkles in the skin using a formulation comprising the L complex of botulinum neurotoxin E.

The fifteenth aspect of the presently claimed invention is directed a method of treating wrinkles in the skin using a formulation comprising the M complex of botulinum neurotoxin E.

The sixteenth aspect of the presently claimed invention is directed to a method of treating one or more of: acute pain, neuromuscular disorder, muscle spasm, excessive sweating, itching in the skin, comprising the step of: administering a formulation of the present invention comprising a complex of botulinum neurotoxin E.

The seventeenth aspect of the presently claimed invention is directed a method of treating acute pain, neuromuscular disorder, muscle spasm, excessive sweating, itch in the skin comprising the step of: administering a composition of the present invention comprising the L complex of botulinum neurotoxin E.

The eighteenth aspect of the presently claimed invention is directed a method of treating one or more of: acute pain, neuromuscular disorder, muscle spasm, excessive sweating, itching in the skin by administering a composition of the presently claimed invention comprising the M complex of botulinum neurotoxin E.

The nineteenth aspect of the presently claimed invention is to a composition and method of treatment comprising the M-complex that demonstrates at least 50% higher endopeptidase activity compared to the isolated type E-neurotoxin.

DESCRIPTION OF THE DRAWINGS

Figures 1A, 1B:
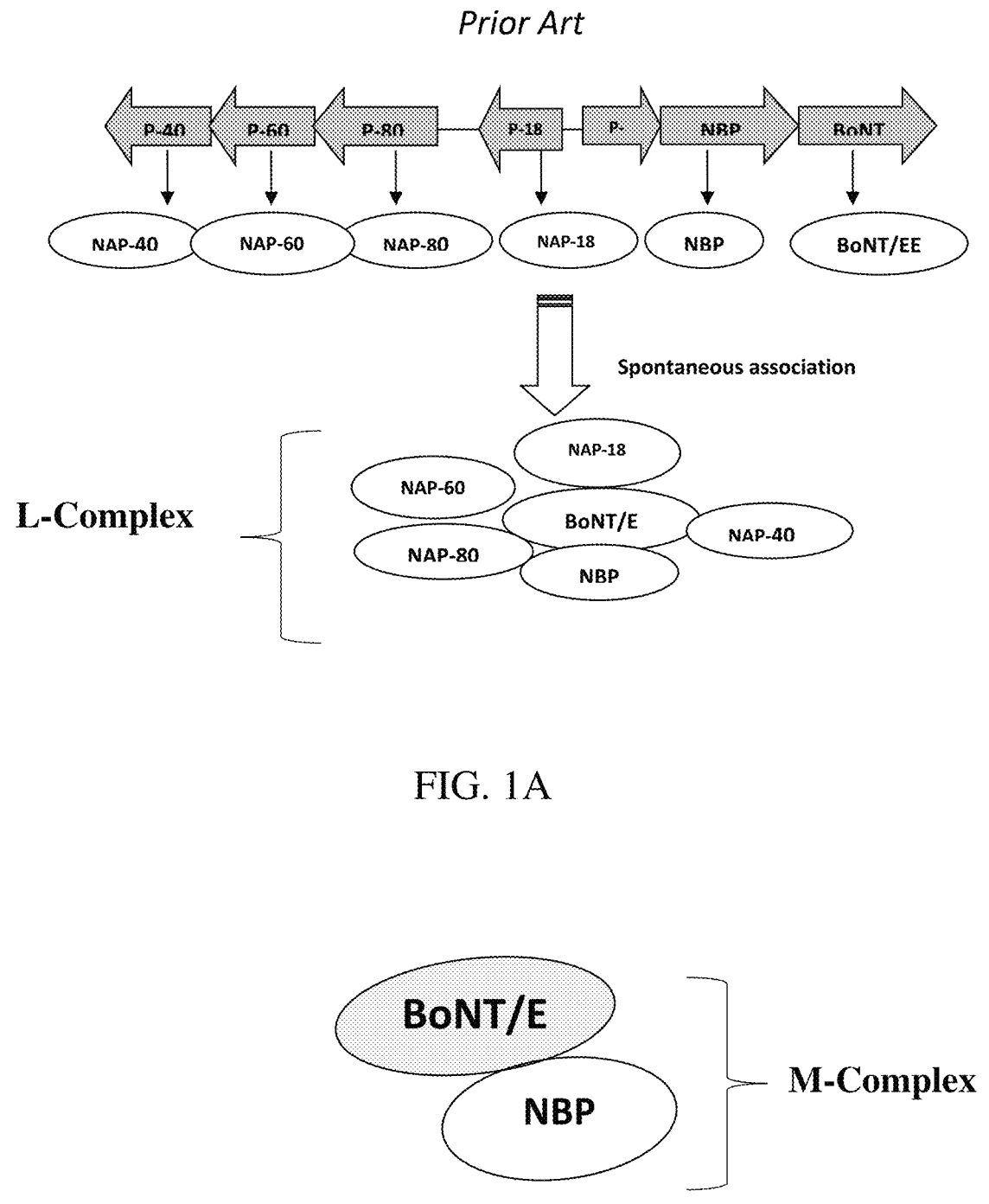

FIG. 1A is a prior art diagram illustrating the plurality of proteins comprising the type E botulinum neurotoxin complex (BoNT/EC), referred herein to as the "L-complex".

FIG. 1B is a prior art diagram illustrating the plurality of "M-complex", which comprises the BoNT/E protein and NBP of the L-complex.

DETAILED DESCRIPTION

Figure 2:
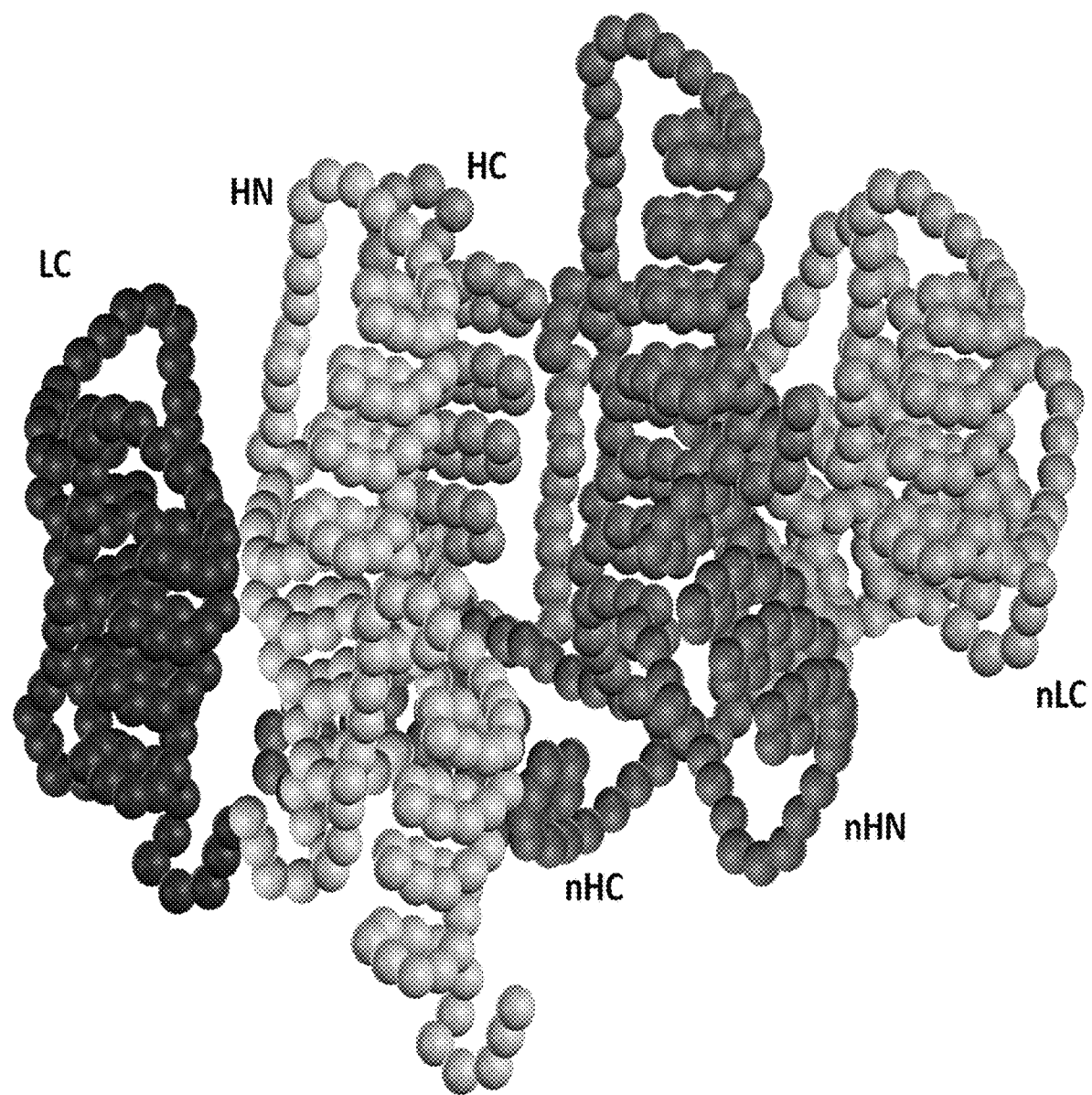
FIG. 2 is an illustration of a Ball representation of the structure of the M-complex. For Botulinum toxin E, LC, HN, and HC are light chain, heavy chain N-terminus, and heavy chain NC-terminus, respectively. Similarly, for the NBP (neurotoxin binding protein), nLC, nHN and nHC are light chain, heavy chain N-terminus and heavy chain C-terminus.

Before the present compositions and formulations of the presently claimed invention are described, it is to be understood that this invention is not limited to particular compositions and formulations described, since such compositions and formulation may, of course, vary. It is also to be understood that the terminology used herein is not intended to be limiting, since the scope of the presently claimed invention will be limited only by the appended claims.

Furthermore, the ranges defined throughout the specification include the end values as well i.e. a range of 1 to 10 implies that both 1 and 10 are included in the range. For the avoidance of doubt, applicant shall be entitled to any equivalents according to applicable law.

In the following passages, different aspects of the presently claimed invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to 'one embodiment' or 'an embodiment' means that a particular feature, structure or characteristic described in connection with the embodiment is included in at least one embodiment of the presently claimed invention. Thus, appearances of the phrases 'in one embodiment' or 'in an embodiment' in various places throughout this specification are not necessarily all referring to the same embodiment but may.

Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the presently claimed invention, and form different embodiments, as would be understood by those in the art. For example, in the appended claims, any of the claimed embodiments can be used in any combination.

In a first embodiment, the presently claimed invention is directed to a composition comprising a complex of botulinum neurotoxin E. More preferably, the composition comprises a L complex of botulinum neurotoxin E, and most preferably, the composition comprises a M complex of botulinum neurotoxin E.

In another preferred embodiment, the complex of botulinum neurotoxin E has secondary structure of 20 to 30% α-helix, 35 to 55% β-sheet, 20 to 35% random coils and 0 to 8% β-turns as determined according to far UV circular dichroism, more preferably the complex of botulinum neurotoxin E has secondary structure of 22 to 28% α-helix, 40 to 50% β-sheet, 22 to 32% random coils and 0 to 5% β-turns as determined according to far UV circular dichroism, most preferably, the complex of botulinum neurotoxin E has secondary structure of 22 to 28% α-helix, 40 to 50% β-sheet, 25 to 30% random coils and 0 to 5% β-turns as determined according to far UV circular dichroism, and in particular, the complex of botulinum neurotoxin E has secondary structure of 25% α-helix, 45% β-sheet, 27% random coils and 3% β-turns as determined according to far UV circular dichroism (Singh and DasGupta, 1989; Singh et al., 1991; Singh et al., 1995).

In another preferred embodiment, the botulinum toxin E has secondary structure of 15 to 30% α-helix, 35 to 55% β-sheet, 25 to 40% random coils and 0 to 8% β-turns as determined according to far UV circular dichroism; more preferably the botulinum toxin E has secondary structure of 18 to 28% α-helix, 38 to 50% β-sheet, 28 to 38% random coils and 0 to 5% β-turns as determined according to far UV circular dichroism; most preferably the botulinum toxin E has secondary structure of 20 to 25% α-helix, 40 to 48% β-sheet, 30 to 38% random coils and 0 to 3% β-turns as determined according to far UV circular dichroism, and in particular the botulinum toxin E has secondary structure of 22% α-helix, 44% β-sheet, 34% random coils and 0% β-turns as determined according to far UV circular dichroism.

In another preferred embodiment, the neurotoxin binding protein (NBP) has secondary structure of 15 to 30% α-helix, 40 to 60% β-sheet, 20 to 40% random coils and 0 to 8% β-turns as determined according to far UV circular dichroism; more preferably the neuro toxin binding protein has secondary structure of 15 to 25% α-helix, 45 to 55% β-sheet, 25 to 35% random coils and 0 to 5% β-turns as determined according to far UV circular dichroism; most preferably the neurotoxin binding protein has secondary structure of 15 to 22% α-helix, 48 to 53% β-sheet, 25 to 30% random coils and 0 to 3% β-turns as determined according to far UV circular dichroism; and in particular the neuro toxin binding protein has secondary structure of 19% α-helix, 50% β-sheet, 28% random coils and 3% β-turns as determined according to far UV circular dichroism (Singh et al., 1995).

In another preferred embodiment, the L complex of botulinum neurotoxin E is botulinum neurotoxin E and its neurotoxin binding protein(s), and M complex of botulinum neurotoxin E is botulinum neurotoxin E and the neurotoxin binding protein(s).

In another preferred embodiment, the complex of botulinum neurotoxin E and neurotoxin binding protein is the M complex.

In another preferred embodiment, the M complex is formed by interactions between or with the neurotoxin binding protein (NBP) and toxin molecule.

In another preferred embodiment, the complex formed between botulinum neurotoxin type E and neurotoxin binding protein has at least 90% higher biological activity than the isolated botulinum neurotoxin type E; more preferably the complex formed between botulinum neurotoxin type E and its neurotoxin binding protein has at least 80% higher biological activity than the isolated botulinum neurotoxin type E, even more preferably the complex formed between botulinum neurotoxin type E and its neurotoxin binding protein has at least 70% higher biological activity than the isolated botulinum neurotoxin type E, most preferably the complex formed between botulinum neurotoxin type E and its neurotoxin binding protein has at least 50% higher biological activity than the isolated botulinum neurotoxin type E, and in particular the complex formed between botulinum neurotoxin type E and its neurotoxin binding protein has at least 50% higher biological activity than the isolated botulinum neurotoxin type E.

In another preferred embodiment, the L complex formed between botulinum neurotoxin type E and its neurotoxin binding proteins has at least 50% higher biological activity than the isolated botulinum neurotoxin type E; more preferably the L complex formed between botulinum neurotoxin type E and its neurotoxin binding protein has at least 40% higher biological activity than the isolated botulinum neurotoxin type E, even more preferably the L complex formed between botulinum neurotoxin type E and its neurotoxin binding protein has at least 30% higher biological activity than the isolated botulinum neurotoxin type E, most preferably the L complex formed between botulinum neurotoxin type E and its neurotoxin binding protein has at least 20% higher biological activity than the isolated botulinum neurotoxin type E, and in particular the L complex formed between botulinum neurotoxin type E and its neurotoxin binding protein has at least 10% higher biological activity than the isolated botulinum neurotoxin type E.

In another preferred embodiment, the M complex formed between botulinum neurotoxin type E and its neurotoxin binding protein has at least 90% higher biological activity than the isolated botulinum neurotoxin type E; more preferably the M complex formed between botulinum neurotoxin type E and its neurotoxin binding protein has at least 80% higher biological activity than the isolated botulinum neurotoxin type E, even more preferably the M complex formed between botulinum neurotoxin type E and its neurotoxin binding protein has at least 70% higher biological activity than the isolated botulinum neurotoxin type E, most preferably the M complex formed between botulinum neurotoxin type E and its neurotoxin binding protein has at least 50% higher biological activity than the isolated botulinum neurotoxin type E, and in particular the M complex formed between botulinum neurotoxin type E and its neurotoxin binding protein has at least 50% higher biological activity than the isolated botulinum neurotoxin type E.

In another preferred embodiment, the M complex formed between botulinum neurotoxin type E and its neurotoxin binding protein has higher biological activity than the complex formed between botulinum neurotoxin type E and its neurotoxin binding protein, the L complex formed between botulinum neurotoxin type E and its neurotoxin binding protein and the isolated botulinum neurotoxin type E.

In another preferred embodiment, the M complex of botulinum neurotoxin E and the neurotoxin binding protein has a molecular weight of in the range of 250 to 300 KDa.

In another preferred embodiment, the complex of botulinum neurotoxin type E and the neurotoxin binding protein is isolated from bacterial culture.

In another preferred embodiment, the L complex of botulinum neurotoxin type E and the neurotoxin binding protein is isolated from bacterial culture.

In another preferred embodiment, the M complex of botulinum neurotoxin type E and the neurotoxin binding protein is isolated from bacterial culture.

In another preferred embodiment, the composition is a "pharmaceutical composition" comprising a formulation in which an active ingredient is the complex of botulinum neurotoxin type E and its neurotoxin binding protein. The word "formulation" means that there is at least one additional ingredient (such as, for example and not limited to: an albumin—e.g. a human serum albumin or a recombinant human albumin; and/or sodium chloride) in the pharmaceutical composition in addition to the complex of botulinum neurotoxin type E and its neurotoxin binding protein. A pharmaceutical composition is therefore a formulation which is suitable for diagnostic, therapeutic or cosmetic administration to a subject, such as a human patient. The pharmaceutical composition can be: in a lyophilized or vacuum dried condition, a solution formed after reconstitution of the lyophilized or vacuum dried pharmaceutical composition with saline or water, for example, or; as a solution that does not require reconstitution. As stated, a pharmaceutical composition can be liquid or solid. A pharmaceutical composition can be animal protein free.

In another preferred embodiment, the term "Fast-acting" as used herein refers to a complex of botulinum neurotoxin type E and its neurotoxin binding protein that produces effects in the patient more rapidly than those produced by, for example, a botulinum neurotoxin type A, or the complex of botulinum neurotoxin type A and its neurotoxin associated protein. For example, the effects of a fast-acting botulinum toxin can be visible within 36 hours.

In another embodiment the presently claimed invention is directed to a method for the isolation of a complex of botulinum neurotoxin type E and its neurotoxin binding protein.

In another preferred embodiment, the solution comprising the complex of botulinum neurotoxin E and its neurotoxin binding protein is obtained according to the steps of Table 1:

TABLE 1 a) provide a bacterial grown in a cultured media comprising complex of botulinum neurotoxin E and its neurotoxin binding protein;
b) grow a Type E culture for 96 hours in a sterilized culture media;
c) centrifuge the culture and pelletizing the cells of step (b);
d) wash the pelletized culture, and disperse it in an extraction buffer;
e) centrifuge the stirred solution of step (d) to obtain a supernatant;
f) precipitate the supernatant (extract-I) to obtain a precipitate by centrifugation;
g) dissolve the precipitate of step (f) in the extraction buffer and keep overnight with stirring; and
h) centrifuge and precipitate the supernatant (extract-II).

In another preferred embodiment, the process comprises the step (d) of:
  d1) wash the pelletized cells with sodium-acetate buffer at a pH in the range of pH 4.5 to 5.5; and
  d2) disperse the pelletized cells in an extraction buffer comprising sodium phosphate buffer at a pH in the range of 5.5 to 6.5.

In another preferred embodiment, the presently claimed invention comprises a step (i) of: mixing the supernatant obtained in step (f) and step (h) to obtain a combined supernatant.

In another preferred embodiment, the solution comprising the complex of botulinum neurotoxin E and its neurotoxin binding protein is obtained according to the steps of Table 2.

TABLE 2 a) provide a bacterial grown in a cultured media comprising a complex of botulinum neurotoxin E and its neurotoxin binding proteins;
b) centrifuge and pelletize the cultured media of step (a);
b1) wash the pelletized cells with sodium-acetate buffer at a pH in the range of pH 4.5 to 5.5;
b2) disperse the pelletized cells in sodium phosphate buffer at a pH in the range of 5.5 to 6.5;
b3) filter the dispersion to obtain a supernatant;
c) stir the pelletized culture at 0 to 10° C. over a period of 4 to 24 hours;
d) centrifuge the stirred solution of step (c) to obtain a supernatant;
d1) mixing the supernatant obtained in step (b3) and step (d) to obtain a combined supernatant;
e) precipitate the supernatant and filter to obtain the precipitate; and
f) dissolve the precipitate obtained in step (e), centrifuge and filter to obtain a solution comprising a complex of botulinum neurotoxin E and its neurotoxin binding protein.

In another embodiment, the presently claimed invention is directed to a method of isolation of the L complex of botulinum neurotoxin E and its neurotoxin binding protein, comprising the steps of: recovering the L complex of botulinum neurotoxin A and neurotoxin binding protein(s) by flowing the solution obtained in Table 2, step (f), through a functionalized sephadex ion exchange column.

In another preferred embodiment, the functionalized sephadex ion exchange bead has a size of 40 to 125 μm.

In another preferred embodiment, the sephadex ion exchange bead is functionalized using 2-(diethylamino)ethyl functionality.

In another embodiment, the presently claimed invention is directed to a method of isolation of the M complex of botulinum neurotoxin E and its neurotoxin binding protein, comprising the steps of: passing a solution of Table 2, step (f), through a functionalized sepharose ion exchange column; and recovering the M complex of botulinum neurotoxin E and neurotoxin binding protein.

In another preferred embodiment, the functionalized sephadex ion exchange bead has a size of 40 to 120μ.

In another preferred embodiment, the sephadex ion exchange bead is functionalized using —O—$CH_2COO^-$ functionality.

In another preferred embodiment, the pH of the overall process is maintained in the range of 4.5 to 7.5.

In another preferred, Table 2, step (c), the solution is stirred in a sodium phosphate buffer at a pH in the range of 5 to 7; and more preferably is stirred in sodium phosphate at a pH in the range of 5.5 to 6.5.

In another preferred, Table 2, step (f), the solution is stirred in a sodium citrate buffer at a pH in the range of 5 to 7; and more preferably in step (f) the precipitate is dissolved in sodium citrate buffer at a pH in the range of 5.0 to 6.5; and most preferably in step (f) the precipitate is dissolved in sodium citrate buffer at a pH in the range of 5.0 to 6.0.

In another embodiment, the presently claimed invention is directed to the use of the composition comprising complex of botulinum neurotoxin E and its neurotoxin binding protein, or the composition comprising the L complex of botulinum neurotoxin E and its neurotoxin binding protein, or the composition comprising M complex of botulinum neurotoxin E and its neurotoxin binding protein in cosmetics; more preferably the presently claimed invention is directed to the use of the composition comprising the L complex of botulinum neurotoxin E and its neurotoxin binding protein, or the composition comprising M complex of botulinum neurotoxin E and its neurotoxin binding protein in cosmetics; and most preferably the presently claimed invention is directed to the use of the composition comprising M complex of botulinum neurotoxin E and its neurotoxin binding protein in cosmetics.

Method of Use

The presently claimed invention is also directed to the use of the composition comprising the complex of botulinum neurotoxin E and its neurotoxin binding protein, or the composition comprising the M complex of the L complex of botulinum neurotoxin E and its neurotoxin binding protein(s) in pharmaceutical formulation(s).

In another embodiment, the presently claimed invention is directed to a method of treating wrinkles in the skin comprising the steps of: administering a composition comprising complex of botulinum neurotoxin E and neurotoxin binding protein, or the composition comprising M complex of botulinum neurotoxin E in pharmaceutical formulation(s). In a preferred embodiment, the M complex is administered.

In another embodiment, the presently claimed invention will be administered through intramuscular (IM), intraperitoneal (IP), subcutaneous (SC) or topical.

In another embodiment, the presently claimed invention will have complex of botulinum neurotoxin E and neurotoxin binding protein, or the composition comprising M complex of botulinum neurotoxin E in a pharmaceutical formulation which comprises excipients such as sodium chloride, human serum albumin, cyclodextrin, lidocaine, histidine as needed either in combination or alone.

In another embodiment, the presently claimed invention is directed to a method of treating acute pain, neuromuscular disorder, muscle spasm, excessive sweating, and itching comprising the steps of administering a composition comprising complex of botulinum neurotoxin E and its neurotoxin binding protein. Specifically, the composition comprising the complex of botulinum neurotoxin E and neurotoxic binding protein, or the composition comprising M complex of botulinum neurotoxin E in pharmaceutical formulation(s). In a preferred embodiment, the M complex is administered.

Experimental Data

FIG. 2 is an illustration of a Ball representation of the structure of the M-complex for use in compositions and methods of the present invention. For Botulinum toxin E, LC, HN, and HC are light chain, heavy chain N-terminus, and heavy chain NC-terminus, respectively. Similarly, for the NBP (neurotoxin binding protein), nLC, nHN and nHC are light chain, heavy chain N-terminus and heavy chain C-terminus.

Figure 3:
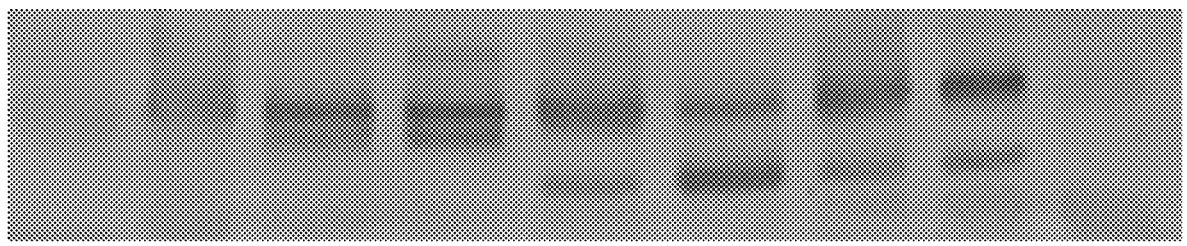
FIG. 3 is an image of a Western blot of SNAP-25 cleavage by different forms of toxin in M-17 cells. Lane 1 (from left) is marker, lane 2 is control cells (untreated), lane 3 is botulinum toxin complex of serotype A treated cells, lane 4 is pure botulinum toxin of serotype A treated cells, lane 5 botulinum toxin complex of serotype E treated cells, lane 6 is botulinum toxin M-complex of serotype E treated cells, lane 7 is pure botulinum toxin (batch-I) of serotype E treated cells, and lane 8 is pure botulinum toxin (batch-II) of serotype E treated cells. Upper band is uncleaved SNAP-25 and lower band is cleaved SNAP-25.

FIG. 3 is an image of a Western blot of SNAP-25 cleavage by different forms of toxin in M-17 cells. Lane 1 (from left) is marker, lane 2 is control cells (untreated), lane 3 is botulinum toxin complex of serotype A treated cells, lane 4 is pure botulinum toxin of serotype A treated cells, lane 5 botulinum toxin complex of serotype E treated cells, lane 6 is botulinum toxin M-complex of serotype E treated cells, lane 7 is pure botulinum toxin (batch-I) of serotype E treated cells, and lane 8 is pure botulinum toxin (batch-II) of serotype E treated cells. Upper band is uncleaved SNAP-25 and lower band is cleaved SNAP-25.

CONCLUSION

It will be appreciated that the methods and compositions of the present disclosure can be incorporated in the form of a variety of embodiments, only a few of which are disclosed herein. It will also be apparent for the expert skilled in the field that other embodiments exist and do not depart from the spirit of the invention. Thus, the described embodiments are illustrative and should not be construed as restrictive.

Accordingly, the preceding exemplifications merely illustrate the principles of the various embodiments. It will be appreciated that those skilled in the art will be able to devise various arrangements which, although not explicitly described or shown herein, embody the principles of the embodiments and are included within its spirit and scope. Furthermore, all examples and conditional language recited herein are principally intended to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the various embodiments, therefore, is not intended to be limited to the exemplary embodiments shown and described herein.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Or, the technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed.

The term "a" or "an" can refer to one of or a plurality of the elements it modifies (e.g., "a reagent" can mean one or more reagents) unless it is contextually clear either one of the elements or more than one of the elements is described.

The term "about" as used herein refers to a value within 10% of the underlying parameter (i.e., plus or minus 5%), and use of the term "about" at the beginning of a string of values modifies each of the values (i.e., "about 1, 2 and 3" refers to about 1, about 2 and about 3). Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

As used herein, the term "substantially" refers to approximately the same shape as stated.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments.

Trademarks: the product names used in this document are for identification purposes only; and are the property of their respective owners.

LIST OF REFERENCES CITED

Binz T, Kurazono H, Wille M, Frevert J, Wernars K, Niemann H. The complete sequence of botulinum neurotoxin type A and comparison with other clostridial neurotoxins. J Biol Chem. 1990a; 265:9153-9158.

Binz, T., Kurazono, H., Popoff, M. R., Eklund, M. W., Sakaguchi, G., Kozaki, S., Krieglstein, K., Henschen, A, Gill, M. D., and Niemann, H. (1990b) Nucleic Acids Res. 18, 5556.

Eswaramoorthy et al. (2015) Molecular Assembly of Clostridium botulinum progenitor M complex of type E. Scientific Reports. 5, 17795: 1-9.

Kumar, R., Chang, T. W., and Singh, B. R. (2013) Evolutionary traits of toxins. Handbook of Toxinology (Editor: P. Gopalakrishnakone, Springer): Biological Toxins and Bioterrorism, Springer Dordrecht Heidelberg New York London, Vol 1, chapter 23, 527-557.

Hauser, D., Eklund, M. W., Kurazono, H., Binz, T., Niemann, H., Gill, M. D., Boquet, P., and Popoff, M. R. (1990) Nucleic Acids Res. 18, 4924.

Li, B., Qian, X., Sarkar, H. K., and Singh, B. R. (1998) Molecular characterization of type E Clostridium botulinum and comparison to other types of Clostridium botulinum, Biochimica et Biophysica. Acta. 1395, 21-27.

Ohishi, I., and Sakaguchi, G. (1980). Oral toxicities of Clostridium botulinum type C and D toxins of different molecular sizes. Infect Immun. 1980 May; 28(2): 303-309.

Ohishi, I., Sugii, S., and Sakaguchi, G. (1977). Oral toxicities of Clostridium botulinum toxins in response to molecular size. Infect Immun., 16, 107-109.

Sakaguchi G, 1983, Clostridium botulinum toxins, Pharmac Therap., 19:165-194.

Schantz E J, Johnson E A (1992) Properties and use of botulinum toxin and other microbial neurotoxins in medicine. Microbiology and Molecular Biology Reviews. 56(1): 80-99.

Singh, B. R., Foley, J., Lafontaine, C. (1995) Physicochemical and immunological characterization of type E botulinum neurotoxin binding protein purified from Clostridium botulinum, J. Protein Chem. 14, 7-18.

Sugii S and Sakaguchi G (1975) Molecular construction of Clostridium botulinum type A toxins. Infect immune 1975. 12:1262-70.

Thompson, D. E., Brehm, J. K., Oultram, J. D., Swinfield, T. J., Shone, C. C., Atkinson, T., Melling, J., and Minton, N. P. (1990). The complete amino acid sequence of the Clostridium botulinum type A neurotoxin, deduced by nucleotide sequence analysis of the encoding gene. European Journal of Biochemistry, 1990 Apr. 20; 189(1):73-81.

Whelan S M, Elmore M J, Bodsworth N J, Atkinson T, Minton N (1992a) The complete amino acid sequence of the Clostridium botulinum type E neurotoxin, deduced by nucleotide sequence analysis of the encoding gene. Eur J Biochem 204:657-667.

Whelan, S., Elmore, M. J., Bodsworth, N., Brehm, J, Atkinson, T., and Minton, N. P. (1992 b). Molecular Cloning of the Clostridium botulinum Structural Gene Encoding the Type B Neurotoxin and Determination of Its Entire Nucleotide Sequence. Applied and Environment Microbiology, 58, 2345-2354.

US Patent Application 20200046814 A1 by Bonti Inc., published Feb. 13, 2020.

U.S. Pat. No. 6,699,966 B1, by University of Massachusetts, published Mar. 2, 2004.

What is claimed is:

1. A pharmaceutical composition comprising:
   a) a pharmaceutical formulation of a M complex of a botulinum neurotoxin E and a neurotoxin binding protein (NBP) associated with the botulinum neurotoxin E;
   b) one or more excipients;
   c) wherein the M complex has at least 70% higher biological activity than the isolated botulinum neurotoxin E alone or alone with any other protein; and
   d) wherein the pharmaceutical composition is stable against denaturation of the M complex to protect it during storage and in vivo.

2. The pharmaceutical composition according to claim 1, wherein the M complex of the botulinum neurotoxin E and the neurotoxin binding protein (NBP) has at least 80% higher biological activity than the isolated botulinum neurotoxin E alone.

3. The pharmaceutical composition according to claim 2, wherein the M complex of the botulinum neurotoxin E and the neurotoxin binding protein (NBP) has a molecular weight in the range of about 250 to about 300 KDa.

4. The pharmaceutical composition according to claim 1, wherein the M complex is isolated from a bacterial culture or is created from a recombinant protein.

5. The pharmaceutical composition according to claim 1, wherein the one or more excipients comprise one or more of: sodium chloride, human serum albumin, cyclodextrin, lidocaine, and histidine, in combination or alone.

6. The pharmaceutical composition according to claim 1, further comprising an appropriate buffer comprising the one or more excipients and one or more stabilizers, to enable the pharmaceutical composition to be administered to effectively treat wrinkles.

7. The pharmaceutical composition according to claim 1, further comprising an appropriate buffer comprising the one or more excipients and one or more stabilizers, to enable the pharmaceutical composition to be administered to effectively treat one or more of: acute pain, chronic pain, neuromuscular disorder, muscle spasm, excessive sweating, gastrointestinal disorders and itching.

8. The pharmaceutical composition according to claim 1, further comprising an appropriate buffer comprising the one or more excipients and one or more stabilizers to enable the pharmaceutical composition to be administered through intramuscular (IM), intra peritoneal (IP), subcutaneous (SC), oral or topical routes.

* * * * *